United States Patent [19]

Nestor et al.

[11] 4,099,521
[45] Jul. 11, 1978

[54] SURGICAL RETRACTOR ADJUSTABLE MOUNTING APPARATUS

[75] Inventors: Jack Nestor; David H. Slepyan, both of Miami Beach, Fla.

[73] Assignee: Nestor Engineering Associates, Inc., Miami, Fla.

[21] Appl. No.: 587,316

[22] Filed: Jun. 16, 1975

[51] Int. Cl.² ............................................. A61B 17/02
[52] U.S. Cl. .................................................. 128/020
[58] Field of Search .................. 128/12, 15, 17, 20, 128/303 R; 403/53, 385, 386, 389, 391, 399; 269/322–328

[56] References Cited

U.S. PATENT DOCUMENTS

| | | | |
|---|---|---|---|
| 2,586,488 | 2/1952 | Smith | 128/20 |
| 2,594,086 | 4/1952 | Smith | 128/20 |
| 2,670,732 | 3/1954 | Nelson | 128/20 |
| 3,046,072 | 7/1962 | Douglass, Jr. et al. | 128/20 X |
| 3,065,981 | 11/1962 | Arrison | 403/385 |
| 3,118,695 | 1/1964 | Engelhardt | 403/53 |
| 3,762,401 | 10/1973 | Tupper | 128/20 |

FOREIGN PATENT DOCUMENTS

| | | | |
|---|---|---|---|
| 350,214 | 11/1905 | France | 128/20 |
| 707,916 | 5/1941 | Fed. Rep. of Germany | 128/12 |

OTHER PUBLICATIONS

"Table Supported Retractor", by O. A. Nelson, Northwest Medicine, Aug. 1952, pp. 676–677.

*Primary Examiner*—Robert W. Michell
*Assistant Examiner*—Henry S. Layton
*Attorney, Agent, or Firm*—Erwin M. Barnett

[57] ABSTRACT

An arcuate frame is sized to fit concentrically at a spaced distance about the head. Retractors, retaining the mouth and lips in open position for vertical and lateral exposure during mouth and jaw surgery, are adjustably suspended from the frame by an adjustable universal connector. The frame is mounted on an upstanding support from the operating table by connecting means providing adjustability thereof for universal spacial orientation. One or more beaded chains control the position and tension on each of the retractors, other than the tongue retractor, by releasably engaging anchors carried by connectors which are adjustably positioned along the frame. A single thumb screw secures and releases each anchor for simultaneous adjustment along the frame and at right angles toward and away from the frame. Other surgical applications requiring adjustable retractors are anticipated for the device.

11 Claims, 14 Drawing Figures

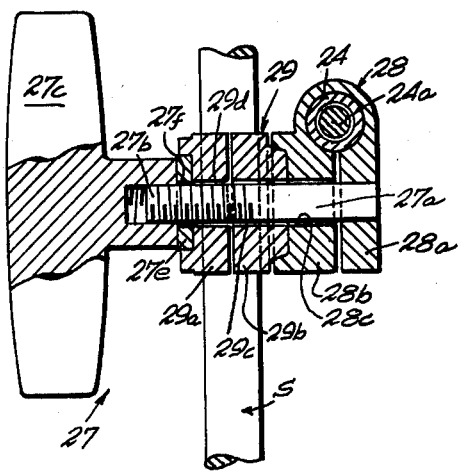
Fig. 3
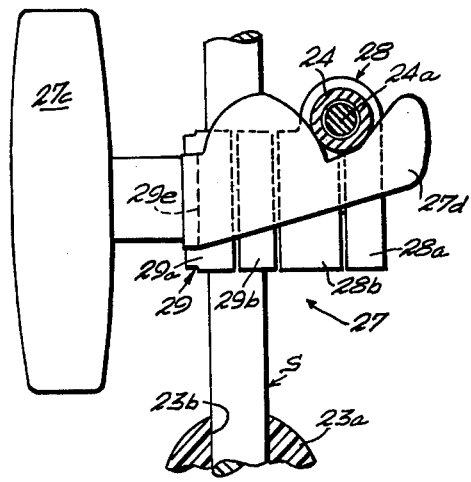
Fig. 4
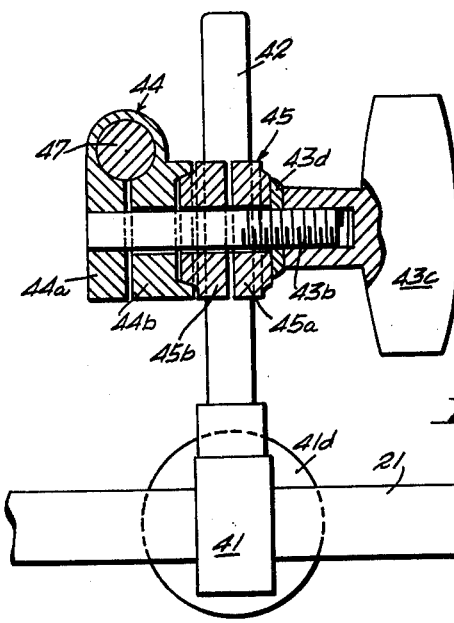
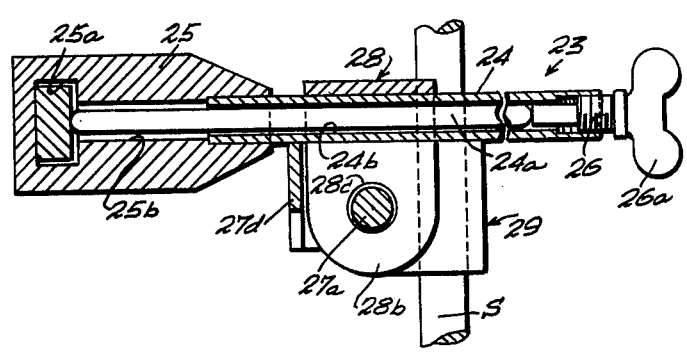
Fig. 6    Fig. 5
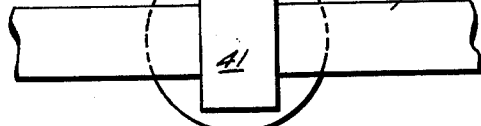
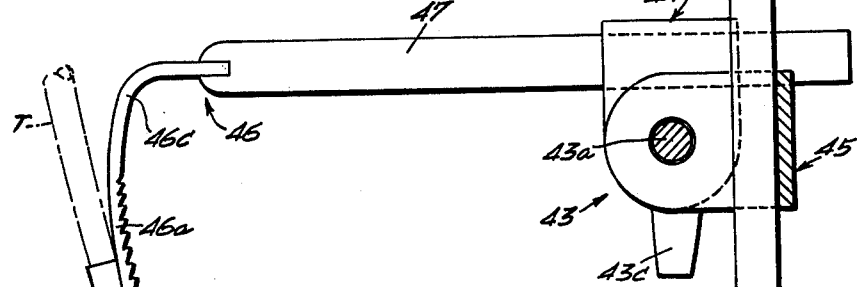
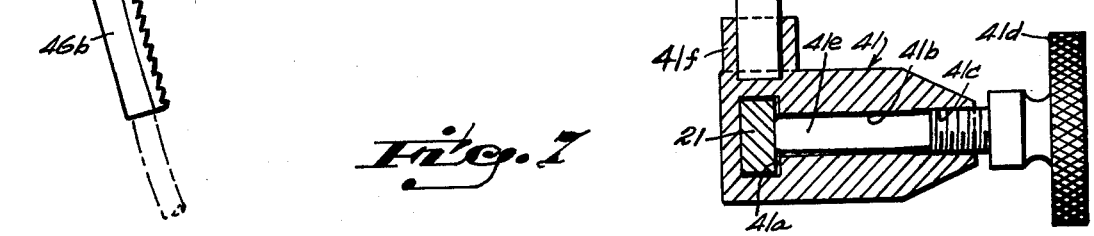
Fig. 7

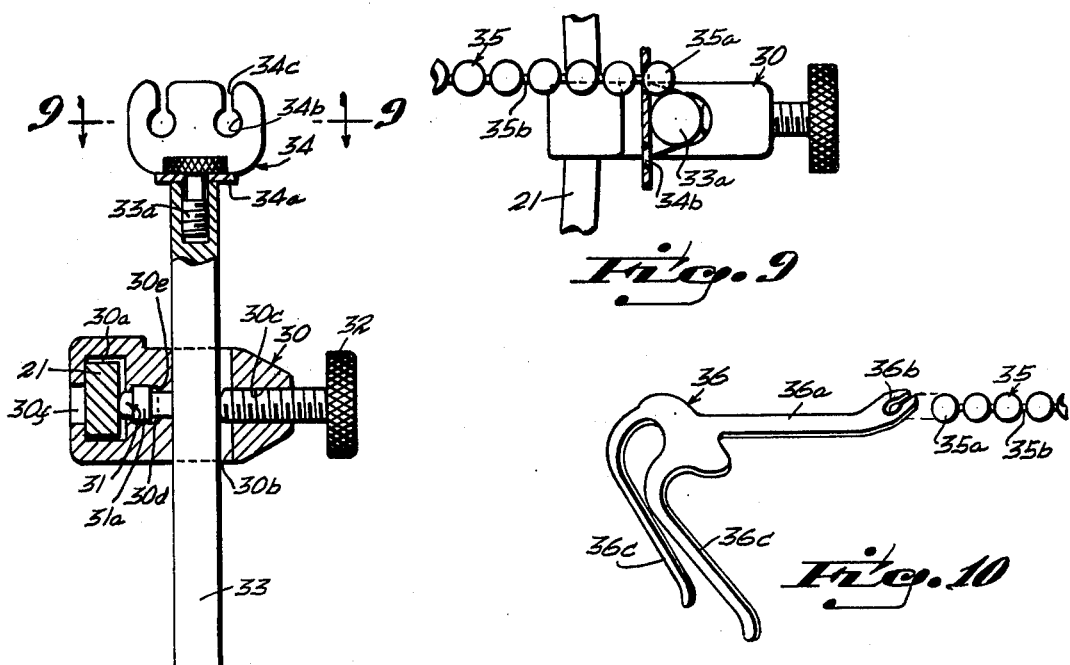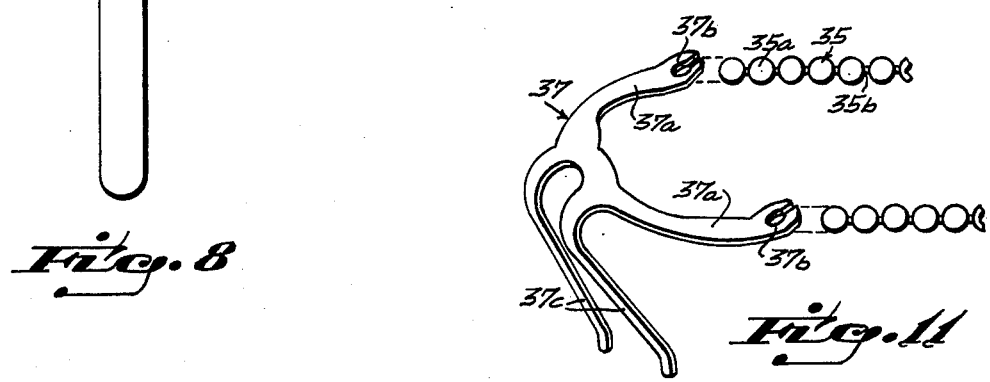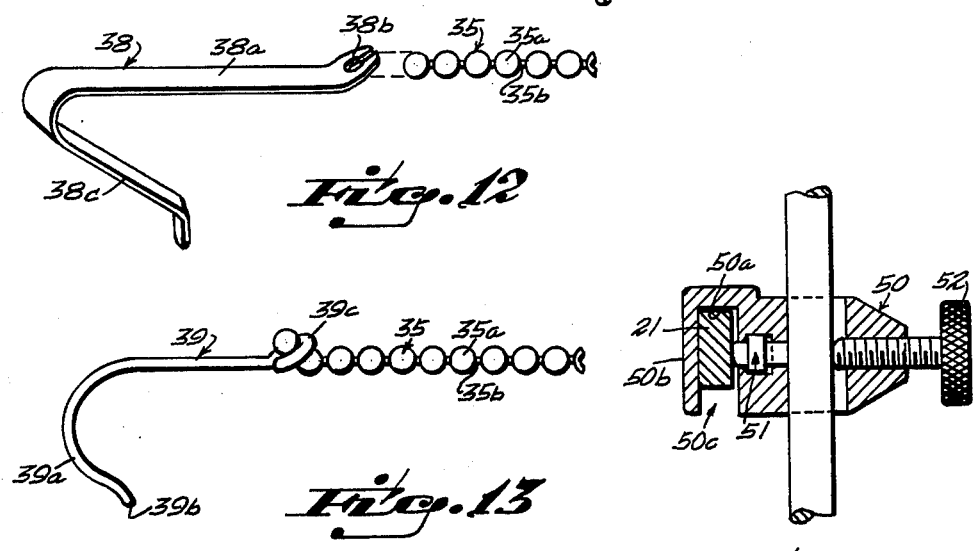

SURGICAL RETRACTOR ADJUSTABLE MOUNTING APPARATUS

BACKGROUND OF THE INVENTION

1. Field of the Invention

The invention relates to a surgical apparatus for retaining and supporting parts of the body in exposed presentation for accessibility by the surgeon while performing an operation thereon. A preferred form of the invention contemplates such apparatus as a mouth gag which is supported independently of the body and affords a wide range of readily accomplished adjustability without the loss of surgical exposure.

2. Description of the Prior Art

The mouth gag in wide use prior to this invention, known as the Dingman mouth gag, has the serious disadvantages of its frame being positioned in such close proximity to the patient's face that it limits the area in which the surgeon and his assistants can work to the extent that the frame actually creates an obstruction, and of the support for the frame being solely derived from the patient's jaw structure. Consequently, exposure by jaw retractors is clumsy, difficult, if not impossible, to adjust during the operation without losing surgical exposure, and limited in scope. Also, the forces exerted ultimately cause additional and undesirable stress to be applied to the patient's jaws. To overcome some of these drawbacks and provide the necessary and adequate exposure, auxiliary retractors have been hand-held by assistants which practice has proven unsatisfactory because of the fatigue factor causing difficulty in applying for any length of time a consistent and uniform force.

There is also an urgent need for a mouth gag for use in facial reconstruction involving an unstable jaw, that is, a jaw hinged at only one side due to injury to or degenerative disease of the other side, also where the patient's teeth and distinct gumline are lacking, and in cases of facial bone grafts in the repair of congenital anomolies, and to support fracture bone fragments while performing a facial repair, the Dingman mouth gag being totally inoperative for such applications.

SUMMARY OF THE INVENTION

Among the objects of the invention is to provide an apparatus for retracting parts of the body to permit relatively free access by the surgeon to the work area and which will eliminate the many disadvantages of prior art devices and prior practices including those hereinbefore described.

The apparatus provides support for the various retractors by a ring which, in the mouth gag embodiment of the invention, is sized to have a major radius in excess of that of the head so as to be capable of surrounding the head at a spaced distance therefrom. The ring is supported independently of the patient's body for universal orientation above or adjacent the member or area undergoing surgery. Lengths of chain, each terminated at one end by a retractor, are releasably anchored to posts which are slidably positioned along the ring and axially movable with respect to the plane of the ring to vary the distance of the anchoring point from the ring.

Rapid adjustability of the effective length of the chain is provided by quick detachable engagement of the links along the chain with an anchoring means on the post while the direction of applied force is likewise quickly adjustable by the manipulation of a single thumb screw operating on a connector between the post and ring. The thumb screw simultaneously releases or locks each post for its movement along the ring and its axial displacement with respect to the plane of the ring. The versatility of the retractors in performing their function are enhanced by their refinement for spacial positioning thereof made possible by the provision and interchangeability of different types of retractors and the use of a double chain type wherein the chains may extend in parallel to a single anchor post or may diverge to a pair of separated posts positioned on the ring. The high degree of adjustability of the anchors and posts permit only as many to be mounted on the ring as is necessary to support the retractors in use. Since any hardware projecting from the ring which is not performing a present function in the operation becomes an obstruction limiting the surgeon's freedom of movement, provision of additional fixed anchors and posts spaced along the ring as an alternative to adjustability is undesirable.

Where positive placement and retention is required, as for example, by a tongue retractor, a post of a slidable connector may carry such retractor for universal orientation in the manner similar to that supporting the ring.

BRIEF DESCRIPTION OF THE DRAWINGS

FIG. 3 is a sectional view taken on line 3—3 in FIG. 2 showing details of the universally adjustable support and horizontal stop for the ring.

FIG. 4 is a sectional view taken on line 4—4 in FIG. 2 showing exterior details of the support and horizontal stop.

FIG. 5 is a sectional view taken on line 5—5 in FIG. 2 showing details of the ring holder shaft assembly.

FIG. 6 is a sectional view taken on line 6—6 in FIG. 2 showing details of the universally adjustable support for the tongue retractor.

FIG. 7 is a sectional view taken on line 7—7 in FIG. 2 showing side view details of the tongue retractor and adjustable support.

FIG. 8 is a sectional view taken on line 8—8 in FIG. 1 showing details of the post and connector assembly.

FIG. 9 is a sectional view taken on line 9—9 in FIG. 8, but with the post rotated 90 degrees and showing a chain secured in the anchor.

FIG. 10 is a perspective view of a double prong single chain retractor.

FIG. 11 is a perspective view of a double prong double chain retractor.

FIG. 12 is a perspective view of a single prong single chain retractor.

FIG. 13 is a perspective view of an alveolus retractor, and

FIG. 14 is a fragmentary sectional view taken similar to FIG. 8 showing a modified form of connector for quick attachment to and removal from the ring.

DESCRIPTION OF THE PREFERRED EMBODIMENT

Referring in detail to the drawings, A generally denotes a surgical apparatus constructed to embody the invention comprising a mouth gag 20 supported for universal orientation by a vertical stanchion S upstanding from a base B which may be removably secured to an operating table by any suitable means, as by a pair of C-clamps C attached to and extending beneath base B. Set screw and knob K permits stanchion S to be disassembled from base B.

Figure 1:
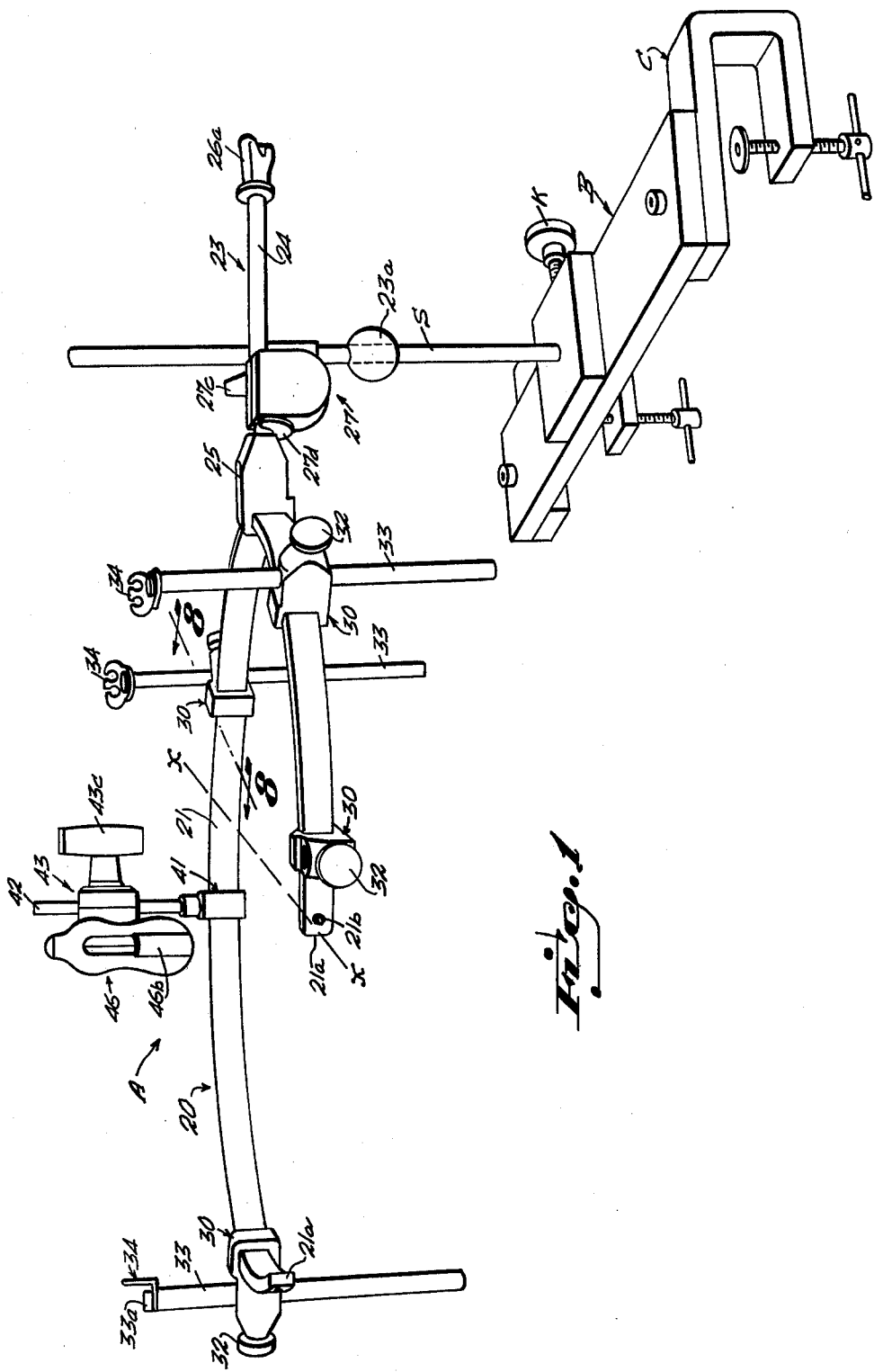
FIG. 1 is a side perspective view of the apparatus embodying the invention showing the ring, a supporting structure for universal orientation of the ring, and various connectors and posts carried by the ring including a tongue retractor and its universal mounting.
Figure 2:
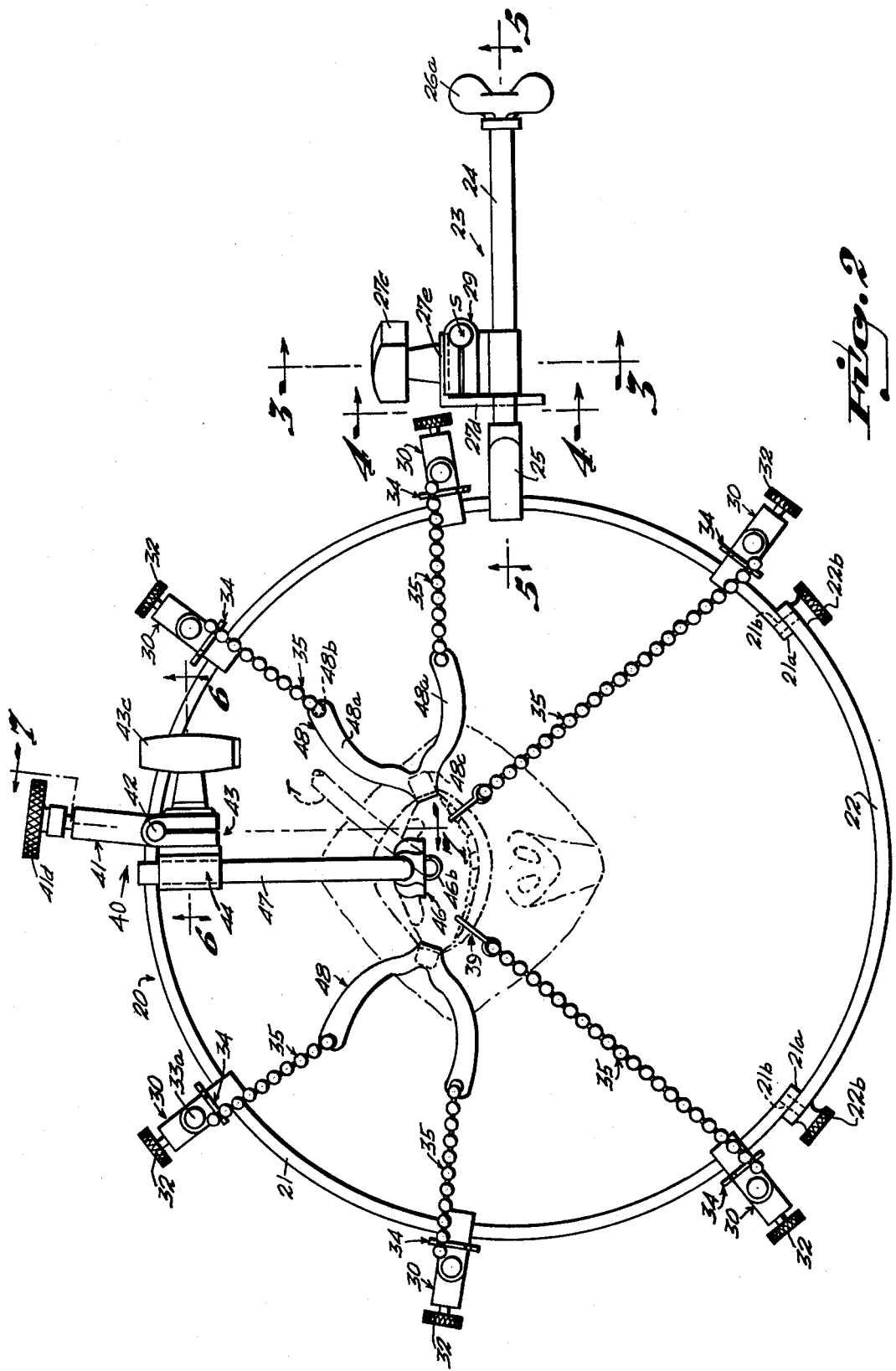
FIG. 2 is a top plan view of the apparatus shown applied as a mouth gag on a patient undergoing surgery, the exposed mouth being shown in broken lines, the face being otherwise covered, the top of the head extending toward the bottom of the figure.

Mouth gag 20 is seen in FIGS. 1 and 2 to comprise an open ring 21, a ring holder shaft assembly 23, a double clamp assembly 27 which adjustably connects shaft assembly 23 to stanchion S providing said universal orientation for ring 21, a plurality of connectors 30 releasably mounted for sliding movement along ring 21, each having an adjustable post 33 provided with a quick connect anchor 34 for beaded chain 35 of retractors 39 and 48, and a tongue retractor assembly 40. Open ring 21 may be formed of bar stock, rectangular in cross-section, and has its greater sectional dimension normal to the plane $x$—$x$ of the ring. A removable arcuate ring section 22, shown in FIG. 2, is sized to overlap the opposite ends 21a of open ring 21 and carries a pair of thumb screw 22b for engaging a pair of threaded openings 21b formed adjacent said opposite ends 21a, whereby ring section 22 attaches to open ring 21 to provide a closed ring structure when so desired.

Ring holder shaft assembly 23 is seen in FIGS. 1, 2 and 5 to be formed with a hollow shaft 24 suitably attached at one end to a slidable connector 25 having a slot 25a through which ring 21 slidably extends. A bore 25b extends at right angles to and opens into slot 25a for accommodating rod 24a which extends through bore 24b of hollow shaft 24 to engage and lock ring 21 in selected position in connector 25 when pressure is applied by tightening screw 26, the latter being threaded into the opposite end of shaft 24 to engage and actuate rod 24a and having a handle 26a sized for convenient manipulation.

Shaft 24 is mounted in clamp 28 of double clamp assembly 27 for longitudinal and rotational adjustability. Clamp 29 in a similar manner engages stanchion S. As shown in FIGS. 3 and 4, clamps 28 and 29 are mounted with their pressure plates 28a, 28b and 29a, 29b, respectively, in juxtaposition for relative rotation on a stub shaft 27a which is press fit or otherwise secured to exterior pressure plate 28a, extends through eyelet 28c in plate 28b and through eyelets 29c and 29d in pressure plates 29b and 29a, respectively, and terminates in threaded end 27b. The latter extends beyond exterior pressure plates 29a for engagement by a large wing nut 27c which, when tightened, simultaneously closes clamps 28 and 29 about shaft 24 and stanchion S, respectively, and tightens interior pressure plate 28b against plate 29b providing sufficient friction therebetween to prevent relative rotation between clamps 28 and 29 on stub shaft 27a. As shown in FIG. 3, the contacting surfaces between interior pressure plates 28b and 29b may be respectively concave and convex. As a safety factor to prevent ring 21 from accidentally pivoting downwardly when double clamp assembly 27 is released for reorientation, stop means 27d extends beneath shaft 24 as it emerges from clamp 28 to limit rotation of the latter on the axis of stub shaft 27a. Stop means 27d has a right angle flange 27e which seats in a cut-out 29e in exterior pressure plate 29a, flange 27e having an opening 27f through which stub shaft 27a projects.

Tongue retractor assembly 40 is shown in FIGS. 1, 2, 6 and 7 to comprise a connector 41 slidably mounted on ring 21, a post 42 upstanding from connector 41 normal to the plane $x$—$x$ of ring 21, and a double clamp assembly 43 which mounts tongue retractor 46 on post 42 for universal adjustability. Tongue retractor 46 has a blade 46a of any well known construction and may be formed with a center channel 46b for receiving a tracheal tube T therein. Blade 46a is connected to one end of shaft 47 by a curved neck 46c for disposition in approximately a right angular relation therewith.

Connector 41 has a slot 41a through which ring 21 slidably extends and a thumb screw pressure exerting means located in bore 41b which extends at right angles to and communicates with slot 41a. Bore 41b is seen to have an internally threaded end 41c which is engaged by thumb screw 41d, the latter having an extension 41e sized to engage and lock ring 21 in slot 41a when tightened.

Post 42 is suitably mounted on connector 41, for example as shown in FIG. 7, press fit or otherwise secured in a boss 41f substantially aligned above slot 41a and ring 21. Double clamp assembly 43 adjustably mounts tongue retractor shaft 47 on post 42 in the same manner as assembly 27 mounts shaft 24 on stanchion S, and thus in FIGS. 6 and 7 is seen to comprise clamp 44 engaging shaft 47, clamp 45 engaging post 42, and having stub shaft 43a on which pressure plates 44a, 44b of clamp 44 and plates 45a, 45b of clamp 45 are mounted, stub shaft 43a being secured to pressure plate 44a so that large wing nut 43c may be tightened or loosened on stub shaft threaded end 43b against washer 43d to lock or release the assembly.

Connectors 30, in a manner similar to connectors 25 and 41, are seen in FIGS. 8 and 9 to each have a slot 30a for being slidably mounted on ring 21. Since it has been found desirable to mount quick connect anchors 34 for chain 35 on a height adjustable means, that is, to provide for varying the distance of anchors 34 from the plane $x$—$x$ of ring 21, posts 33 are axially slidably and rotatably mounted in passageways 30b formed in connectors 30 rather than being fixedly secured in the manner of post 42 on connector 41. To reduce the locking means for connector 30 on ring 21 and for posts 33 in passageways 30b to a single manipulatable means, namely, thumb screw 32, connectors 30 are each formed with a threaded bore 30c extending at right angles to and communicating with passageway 30b, the latter being elliptical in cross-section to permit movement of post 33 towards and away from slot 30a. An intermediate bore 30d interconnects slot 30a with passageway 30b and seats therein a movable pin 31 which is sized to project beyond both ends thereof. To facilitate assembly and to retain pin 31 for its limited movement in bore 30d, the latter is formed with a reduced cross-section adjacent passageway 30b providing a shoulder stop 30e against which an enlarged diameter intermediate portion 31a of pin 31 abuts for limited movement of the latter into passageway 30b. An opening 30f in the exterior wall of slot 30a is sized to accommodate pin 31 for initial insertion into bore 30d which is then swaged at its end adjacent slot 30a. Thumb screw 32 when tightened in bore 30c projects into passageway 30b urging post 33 toward slot 30a to engage pin 31 forcing the latter against ring 21.

Posts 33 are provided at the upper end thereof with suitable anchoring means for beaded chains 35 enabling the effective length of the latter to be quickly varied. Each of such anchors 34 may be permanently attached to a post 33 in any suitable manner or, as shown in FIG. 8, may be removably attached by a screw 33a extending through horizontal flange 34a of anchor 34 which comprises a flat vertically extending plate having one or more openings 34b sized and having a concave border portion to cradle a bead 35a of chain 35, each opening 34b having an entrance slot 34c through which bar link 35b of chain 35 passes.

Retractors 36, 37 38 and 48 are each formed of sheet metal stock to provide flat prongs and attachment bars with smooth rounded edges. Retractors 48, shown in FIG. 2 in use as cheek retractors, each have a double attachment bar 48a projecting as two horns in a semi-circular configuration each terminating in an upturned end formed with a slotted opening 48b for connecting to one end of a chain 35. A single prong 48c, centered with respect to bar 48a, curves downwardly and extends slightly rearwardly, terminating in a blunt downwardly bent end in the manner clearly shown in FIGS. 10 and 11 for prongs 36c and 37c. Retractors 36 and 37 are double prong versions of retractor 48 where additional effective retractor width is required. Retractor 36 has a single attachment bar 36a terminating in slotted opening 36b and retractor 37 has a double attachment bar 37a with slotted openings 37b similar to those of retractor 48. FIG. 12 shows a simple retractor 38 having a single attachment bar 38a with slotted opening 38b and a single prong 38c.

Retractors 39, shown in detail in FIG. 13 and in use as alveolus retractors in FIG. 2, are each formed of wire stock bent into a hook configuration with a curved portion 39a having a blunt end 39b and an attachment portion terminating in a looped eyelet 39c engaging one of chain 35.

The upward bend in each of the attachment bars 36a, 37a, 38a and 48a located inwardly of the respective slotted openings 36b, 37b, 38b and 48b which positions the connecting end of each of the chains 35 above the plane of its said attachment bar has been found to exert a downward component of force on the respective prongs 36c, 37c, 38c and 48c thereby preventing the latter from riding up and out of the mouth when a pulling force is applied to chain 35. The upward bend of looped eyelet 39c of retractor 39 performs a similar function.

In addition to stop means 27d, suitable means may also be provided as a safety device to prevent the accidental vertical dropping of double clamp assembly 27 and the entire mouth gag 20 should clamp 29 inadvertently slide downwardly along stanchion S. To this end, a ball-shaped slider 23a, which may be made of a resinous plastic material, such as, nylon, polyethylene, or the like, is provided with an axial bore 23b sized to friction fit on stanchion S, permitting sliding adjustment therealong but being sufficiently tight to remain firmly in position to perform its intended function as a safety device.

The operation of apparatus A will now be apparent. The various parts having been disassembled and sterilized in an autoclave, apparatus A is reassembled in a configuration to meet the particular needs of the surgical procedure to be performed, but not necessarily in the illustrative sequence hereinafter described. Base B having stanchion S secured thereto by knob and set-screw K may first be attached to the operating table by C-clamps C. Ring holder assembly 23, which in most instances would be intact for sterilization, may then be connected to ring 21 by passing one ring end 21a through slot 25a of connector 25 until assembly 23 is in a desired position on ring 21 and securing the parts by tightening screw 26 by its handle 26a forcing rod 24a to engage ring 21. After positioning slider 23a on stanchion S at a predetermined desirable level, large wing nut 27c of double clamp assembly 27 may be loosened sufficiently for clamp 29 to slide onto stanchion S mounting ring holder assembly 23 and ring 21 thereon above slider 23. The weight of ring 21 normally disposes shaft 24 horizontally as shown in FIG. 1, being retained in this position by stop means 27d.

A plurality of connectors 30 and connector 41 of tongue retractor assembly 40 may then be mounted in desired sequence on ring 21 by inserting a ring end 21a through slots 30a and 41a, respectively. Tongue retractor assembly 40 may be in complete disassembly, that is, double clamp 43 removed from both post 42 and tongue retractor shaft 47, or it may be held intact during sterilization. Partial disassembly wherein only tongue retractor shaft 47 is removed from clamp 44, may be preferable where tongue retractors of various sizes and configurations are provided for selective mounting in clamp 44. Manipulation of wing nut 43c permits clamp 45 to be mounted on post 42 and shaft 47 to be mounted in clamp 44. Tightening thumb screw 41d secures tongue retractor assembly 40 in its selected position on ring 21 and, after posts 33 are inserted into passageways 30b, tightening thumb screws 32 secure connectors 30 in their selected positions on ring 21.

Loosening and tightening large wing nut 27c permits universal adjustment and securing of mouth gag 20 in a desired position. Mouth gag 20 may be raised and lowered on stanchion S, moved toward and away from stanchion S by sliding shaft 24 through clamp 28, rotated on shaft 24 to dispose plane x—x of ring 21 at any angle with respect to the table, rotated on stanchion S and rotated on stub shaft 27a to change the angular relation between stanchion S and shaft 24 but being limited from tilting downwardly by stop means 27d.

As illustrated in FIG. 2, ring 21 is brought into a horizontal position substantially concentric with the head and at a convenient level above the face which may be covered by sheets except for the mouth region. Tongue retractor blade 46a may then be applied to the patient's tongue by first bringing assembly 40 into alignment with the mouth, set screw 41d releasing connector 41 for sliding along ring 21, and then competing fine adjustments of double clamp assembly 43, namely, by loosening wing nut 43c to permit tongue retractor shaft 47 to slide axially through clamp 44 for moving blade 46a toward or away from post 42 or to rotate therein and to swing in both a plane parallel to plane x—x of ring 21 by rotating on post 42 and in a plane at right angle thereto by rotating on stub shaft 43b. Retractors 39 may then be applied to the alveolus and proper tension maintained by anchoring end portions of chains 35 in openings 34b of anchors 34 on the uppr ends of appropriately located posts 33. In addition to the vertical exposure provided by tongue blade 46a and retractors 39, lateral exposure is seen as provided by a pair of retractors 48 placed in the corners of the mouth to retract the cheeks. While a single prong, single attachment bar retractor 38 may be used as a cheek retractor, FIG. 2, in the use of retractors 48, illustrates the manner in which the diverging double chains, each of which may have tension applied and be anchored independently of the other, provide a more precise adjustability.

Readjustment in the form of repositioning of one or more of the retractors or adjusting the tension thereon is easily and rapidly accomplished during the operation without losing surgical exposure by loosening thumb screw 32 to simultaneously slide connector 30 along ring 21 and raise or lower post 33 in passageway 30b and by releasing and repositioning chain 35 in opening 34b of anchor 34. The manipulation of thumb screw 32 and the adjustment of connector 30 and post 33 with a little practice may be performed with one hand. By loosening wing nut 43c, tongue blade 46a may likewise be readjusted during the operation without the loss of surgical exposure.

Removable arcuate ring section 22, having the same cross-sectional dimensions as ring 21, may also be used to slidably carry one or more connectors 30 or 41, one or both thumb screws 22b being removable to permit insertion of an end of section 22 through slots 30a and 41a. Omission of ring section 22 provides an often desirable side approach and access to the work area.

A modified connector 50 is shown in FIG. 14 to comprise thumb screw 52, pin 51 and slot 50a similar to thumb screw 32, pin 31 and slot 30a of connector 30 but differing in that slot 50a has an end wall 50b and an open bottom 50c for slipping directly onto any edge portion of ring 21, permitting rapid addition or removal of a connector and its post to or from ring 21 during the operation. Connector 41 of tongue retractor assembly 40 may be modified in a similar fashion.

It will be understood that within the scope of the disclosure the term chain means shall include, in addition to beaded chain 35, a rope or cable having spaced knots and the like, or a chain having links of any suitable configuration for selectively releasably engaging an anchoring structure on posts 33. Where desirable, the chain means may be attached to retractors 36, 37, 38 or 48 in the manner illustrated or by any other means enabling separation therefrom, or may be permanently connected by welding, clamping or the like.

The surgical apparatus and mouth gag herein disclosed are seen to achieve the several objects of the invention and to be well adapted to meet conditions of practical use. As various possible embodiments might be made of this invention, and as various changes might be made in the disclosed apparatus, it is to be understood that all matters herein set forth or shown in the accompanying drawings are to be interpreted as illustrative and not in a limiting sense.

What is claim is:

1. A surgical apparatus comprising a ring sized to substantially surround a work area at a spaced distance therefrom, a first means adjustably supporting the ring in a position adjacent the work area in concentric relation thereto, a plurality of connectors, each slidably mounted on the ring and having a post slidably mounted for axial movement therethrough in angular relation to the plane of said ring, a quick releasable anchoring means secured to each post, a plurality of retractors, one for engaging each part of the body to be withdrawn, a length of chain means connected to each retractor and adapted for engaging said anchoring means whereby the length of chain means between each retractor and its anchor means is selectively lengthened and shortened, each connector having a quick release means for simultaneously manually releasing and securing each connector in a selected position on the ring and its post in a selected position in the connector to adjust the position of said anchoring means and the direction of force exerted by the chain means on the retractor.

2. The surgical apparatus defined in claim 1, another retractor having a blade supported by a shaft, another connector slidably mounted on the ring and having a second means adjustably supporting said other retractor by the shaft to dispose said blade in a selective positive position in said work area.

3. The surgical apparatus defined in claim 1, in which said first adjustable supporting means includes a stanchion upstanding from an operating table which supports said work area, a ring holder shaft assembly terminating at one end in said ring, and a double clamp assembly adjustably mounting said ring holder shaft assembly on said stanchion.

4. The surgical apparatus defined in claim 1, in which some of said retractors are each formed of sheet metal with a flat attachment bar extending substantially in one plane, a prong curving downwardly and rearwardly from one end of said attachment bar, and an opposite end of the attachment bar being upturned out of said plane and formed with a slotted opening engaging said chain means as said connection thereto whereby tension applied to said chain means exerts a downward component of force on said prong preventing the latter from riding up out of engagement with its said body part.

5. A surgical apparatus having a ring sized to substantially surround a work area at a spaced distance therefrom, a vertical stanchion upstanding from an operating table which supports said work area, a ring holder assembly having a shaft terminating at one end in said ring, a double clamp assembly adjustably mounting said ring holder shaft on said stanchion, said ring holder assembly and double clamp assembly cooperating to suspend said ring in a selective position above said work area in concentric relation thereto, said double clamp assembly having a pair of clamps mounted in juxtaposition for relative rotation on a stub shaft, one clamp engaging said stanchion for axial movement and rotation, the other clamp engaging said ring holder shaft for axial movement and rotation, a wing nut threaded on one end of said stub shaft to simultaneously tighten said clamps about said stanchion and ring holder shaft and to prevent said relative rotation between said clamps, a plurality of quick releasable anchoring means carried by said ring, a plurality of retractors, one for engaging each part of the body to be withdrawn, a length of chain means connected to each retractor and adapted for engaging said anchoring means whereby the length of chain means between each retractor and its anchoring means is selectively lengthened or shortened.

6. The surgical apparatus defined in claim 5, stop means adjustably mounted on said stanchion beneath said double clamp assembly, said stop means being a ball-shaped slider of resinous plastic material having an axial bore sized to friction fit said stanchion permitting sliding adjustment therealong and being sufficiently snug to remain firmly in position against contact by dropping of said double clamp assembly.

7. The surgical apparatus defined in claim 5, in which said ring holder shaft is hollow and terminates at said first end in a slidable connector having a slot through which said ring extends, said slot having an opening communicating with the hollow of said shaft, thumb screw means threaded into the opposite end of said shaft and extending through said hollow and into said slot to engage and lock the ring in a selected position in said slot.

8. The surgical apparatus defined in claim 5, stop means mounted on said first mentioned clamp and extending to engage said ring holder shaft mounted in said other clamp to prevent said relative rotation between said clamps beyond a predetermined angular relation of said ring holder shaft with respect to said stanchion.

9. A surgical apparatus comprising a ring sized to substantially surround a work area at a spaced distance therefrom, a first means adjustably supporting the ring in a position adjacent the work area in concentric relation thereto, a plurality of connectors, each slidably mounted on the ring and carrying a quick releasable anchoring means, a plurality of retractors, one for engaging each part of the body to be withdrawn, a length of chain means connected to each retractor and adapted for engaging said anchoring means whereby the length of chain between each retractor and its anchoring means is selectively lengthened or shortened, one of said retractors being connected by two independent lengths of chain means to two separate connectors spaced apart on said ring.

10. A surgical apparatus comprising a ring sized to substantially surround a work area at a spaced distance therefrom, a first means adjustably supporting the ring in a position adjacent the work area in concentric relation thereto, a plurality of connectors, each slidably mounted on the ring and carrying a quick releasable anchoring means, a plurality of retractors, one for engaging each part of the body to be withdrawn, a length of chain means connected to each retractor and adapted for engaging said anchoring means whereby the length of chain between each retractor and its anchoring means is selectively lengthened or shortened, said ring being formed as an open structure having a removable arcuate ring closing section, whereby removal of the latter provides access to said work area.

11. A surgical retractor of sheet metal comprising a flat attachment bar disposed substantially in one plane, a prong for engaging a body part curving downwardly and rearwardly from one end of said attachment bar, and an opposite end of the attachment bar being formed with two horns in a semi-circular configuration, each horn terminating in an end upturned out of said plane, each upturned end being formed with a slotted opening for engaging a separate tension applying chain whereby the tension applied to said chains, when the retractor prong is in engagement with a body part, exerts a downward component of force on said prong preventing the latter from riding up out of said engagement.

* * * * *